United States Patent [19]

Skrgatic et al.

[11] Patent Number: 4,959,228

[45] Date of Patent: Sep. 25, 1990

[54] MEASUREMENT OF SPECIFIC GRAVITY DURING FERMENTATION

[75] Inventors: Damir M. J. Skrgatic, Edinburgh; James C. Mitchinson, Dunfermline; John A. Graham, Edinburgh, all of Great Britain

[73] Assignee: Acumet Precision Instruments Limited, Edinburg, Scotland

[21] Appl. No.: 436,096

[22] Filed: Nov. 13, 1989

Related U.S. Application Data

[63] Continuation of Ser. No. 70,849, Jul. 31, 1987, abandoned.

[30] Foreign Application Priority Data

Oct. 29, 1985 [GB] United Kingdom ................ 8526628

[51] Int. Cl.$^5$ .................. C12C 11/00; G01N 9/00
[52] U.S. Cl. .................................. 426/11; 426/431; 73/32 A; 73/32 R
[58] Field of Search ................ 426/11, 231; 73/32 R, 73/32 A, 452; 137/91

[56] References Cited

U.S. PATENT DOCUMENTS 3,952,761   4/1976   Friedland ............................... 73/452
4,442,700   4/1984   Swoboda ............................ 73/32 A

*Primary Examiner*—Marianne Cintins
*Attorney, Agent, or Firm*—Ratner & Prestia

[57] ABSTRACT

A method of determining the specific gravity of a fermentable liquor during fermentation is disclosed. Specific gravity is determined from measurements of original gravity, velocity of sound, and temperature.

6 Claims, 5 Drawing Sheets

MEASUREMENT OF SPECIFIC GRAVITY DURING FERMENTATION

This application is a continuation of application Ser. No. 070,849 filed 7/31/87; now abandoned.

This invention relates to a method and apparatus for measuring the specific gravity (s.g.) of liquids. It is of particular utility in relation to brewing, distilling and other processes for producing material for human consumption, but is not limited thereto.

Measurement of s.g. is of great interest in monitoring and controlling brewing and distilling processes. Conventionally, such measurement is done by physically removing a sample for test in a hydrometer or a more sophisticated instrument. It is desirable to replace such measurement by an on-line measurement which could be made part of a process control loop. One object of the present invention is to make this possible.

Accordingly, one aspect of the invention provides a method of measuring the s.g. of a liquid, comprising measuring the velocity of sound in the liquid, measuring the temperature of the liquid, and deriving from these the s.g. of the liquid.

From another aspect, the invention provides apparatus for measuring the s.g. of a liquid, comprising an ultrasonic pulse transimitter and receiver separated by a known path length, means for establishing the transit time of pulses between the transmitter and receiver, a temperature sensor for measuring the temperature of the liquid, and computing means arranged to derive from the transit time and the temperature the s.g. of the liquid.

In preferred forms, the transmitter, receiver and temperature sensor are positioned on the exterior of the liquid container, which may be a storage container such as a tank, or a conduit in which the liquid is flowing.

A relatively simple form of the invention is useful in measuring the s.g. of single-phase solutions such as water/ethanol, for example in whisky distilling. Other embodiments of the invention have utility in measuring the s.g. of more complex solutions and solutions containing gas bubbles and/or solids, for example in brewing.

It will be understood that the apparatus may be used to give a direct reading of a parameter related to s.g., such as the concentration of an acid.

Embodiments of the invention will now be described, by way of example, with reference to the accompanying drawings, in which.

Figure 1:
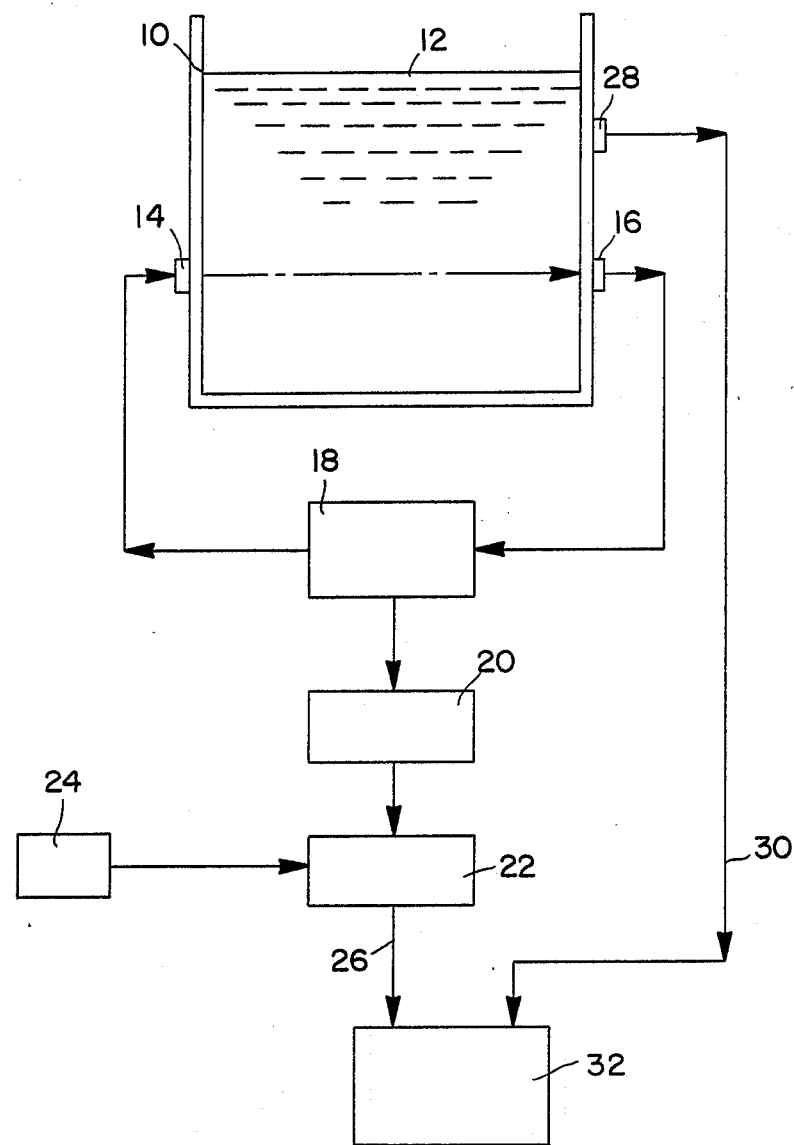
FIG. 1 is a schematic block diagram of one apparatus embodying the invention.

Referring to FIG. 1, a tank 10 holds a liquid 12 the s.g. of which is to be measured. The apparatus includes an ultrasonic transmitting transducer 14 and receiving transducer 16. A pulse generator 18 is connected to drive the transmitting transducer 14 immediately after the preceding pulse has been received at 16.

The arrangement is such that the time taken for a given number of pulses to traverse across the fixed space between the transducers 14 and 16 can be measured from which a measure of the velocity of sound in the liquid 12 can be derived. For this purpose the pulse generator drives a counter 20 to give an output when the predetermined number of pulses has traversed the circuit. The output of the counter 20 is used to reset a counter 22 receiving clock pulses from a clock curcuit 24. Thus the output of counter 22 on line 26 is a measure of the time taken for transit of this number of pulses, which is representative of the sonic velocity.

Alternatively, the transmitter and receiver transducers could be located together, or a single transducer used for both purpose, with the pulses being reflected from the opposite wall of the tank.

The apparatus further includes a temperature sensor 28 giving a signal on line 30 representative of the temperature of the liquid 12. The temperature sensor 28 is suitably a thermistor. It has been found that an accurate measure of the temperature of the contents can be made by a thermistor applied to the exterior of the tank provided that the tank wall of sufficiently low thermal conductivity material and is relatively thin (one example being ⅛ inch stainless steel) and the thermistor is enclosed in thermally insulating material, to minimise the effect of ambient air temperature.

The signals on lines 26 and 30 are supplied to a computing means such as a microprocessor 32 which is arranged to compute the specific gravity of the liquid 12. The speed of sound in the liquid is a function of temperature, specific gravity, and compressibility, and since compressibility is for all practical purposes constant for a liquid the s.g. can be computed given knowledge of the sonic velocity and temperature.

The ouput signal from the microprocessor 32 representing s.g. can be displayed or can be used in a process control loop.

It will be noted that in the drawing the transducers 14 and 16 are shown as being external to the tank 10. This is desirable when one is dealing with substances for human consumption or with substances which are dangerous or corrosive. A technique for permitting such transducers to function via the wall of the tank is fully described in our patent publication No. WO84/01233.

The above embodiment may be modified to minimise the effect of drift and ambient variations in the electronics. As decribed in our patent publication No. EP 0037196 such modification makes use of a reference path through a medium other than the liquid 12 of interest.

It has been found that the above embodiment provides excellent results in measuring the s.g. of pure liquids and single-phase solutions such as ethanol and water. However, determining the s.g. of multi-phase solutions (e.g. water/ethanol/sugar) and liquids containing gas bubbles or solids presents difficulties.

One example of this is beer. When fermenting beer one starts with a material which is essentially a solution of sugars in water. Fermentation converts all, or more commonly only some, of the sugars to ethanol, and thus during fermentation a three-phase solution is present. Additionally, during fermentation carbon dioxide gas is evolved at a varying rate and yeast solids are present in varying amounts. The above embodiment has been found not to give useful measurements of actual s.g. in these circumstances.

The applicants have, however, made the unexpected discovery that the above technique can provide an accurate measure of the original gravity of a beer after fermentation. The term "original gravity" (o.g.) denotes the specific gravity of the liquid before fermentation, and is a measure of the amount of sugars present and thus also of the potential alcohol content if these sugars were to be fully fermented to alcohol. A typical beer o.g. would be 1.035, which in the United Kingdom would conventionally be described as "o.g. 1035". A further term used hereinafter is "product gravity" (p.g.) which refers to the specific gravity of the beer after brewing.

Figure 2:
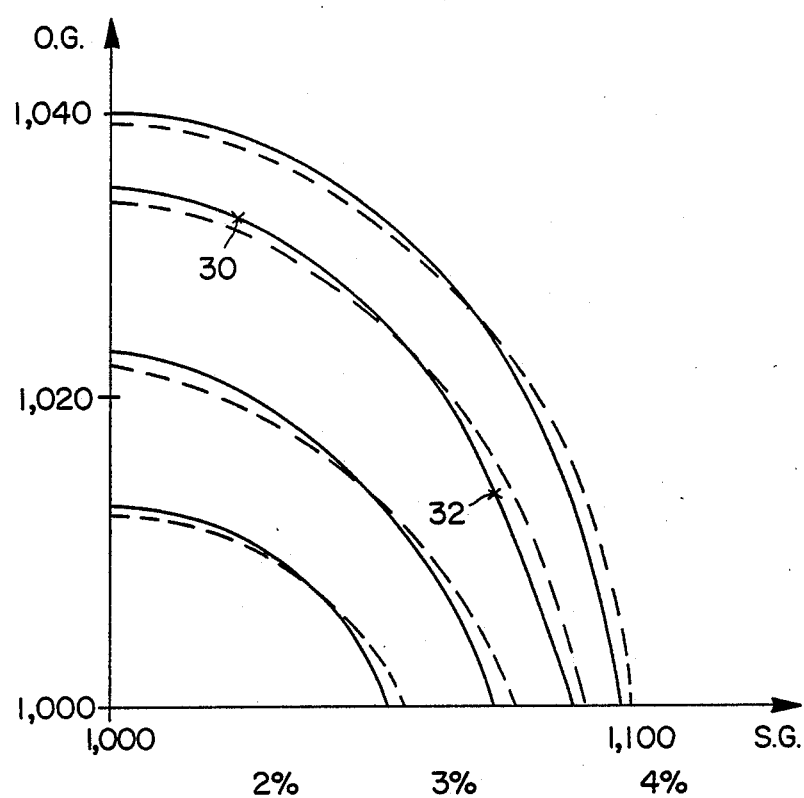
FIG. 2 is a set of graphs representing the relationship between original gravity and specific gravity for beers and the speed of sound therein.

Referring to FIG. 2, there is shown in full lines a family of curves showing the s.g. for beers of various o.g. as they progress from unfermented to fully fermented (assuming constant temperature). As one example, the curve 30 represents a beer with an o.g. of 1.035 which, if totally fermented, results in a beer of s.g. 0.97 approximately. If, however, fermentation is stopped at the point 32, a beer of s.g. approximately 1.008 is obtained, some sugars remaining unfermented. The dashed lines in FIG. 2 represent constant sonic velocities (in the absence of gas and solids) and it will be seen that these follow s.g. closely, but not precisely. Thus, if sonic velocity alone is known, it is possible to derive the o.g. of the liquid but not the actual s.g. which may lie anywhere along the curve. The small differences between the constant o.g. and the constant sonic velocity curves may readily be allowed for by building up a library of curves of empirical methods. This data may suitably be set up in cumputer memory and the computer programmed to make the correction, using interpolation techniques where necessary.

Normally, the o.g. of a brew is known since this is measured by hydrometer before fermentation is started; the apparatus of the present invention can equally be used to measure o.g. Thus, the relationship illustrated in FIG. 2 allows the known o.g. and the measured sonic velocity to be used in principle to derive the s.g. at the time of measurement. Embodiments of the invention making use of this will now be described.

Figure 3:
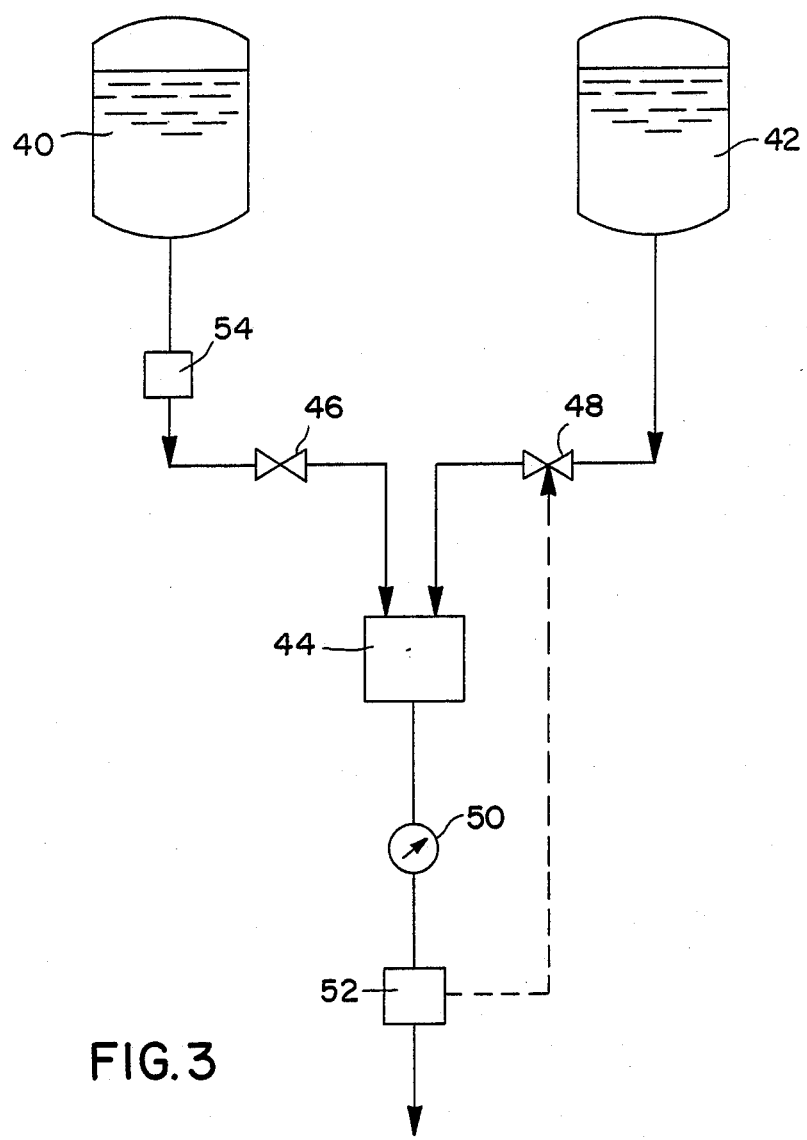
FIG. 3 is a schematic diagram of an apparatus for diluting beer incorporating a monitor embodying the invention.

FIG. 3 illustrates an embodiment in which the above factors are utilised to control a dilution or "cutting" process for beer. It is commercially attractive to brew beer to high strength and thereafter dilute it, but it is necessary to control the dilution to give a product equivalent to a stated o.g.

Figure 4:
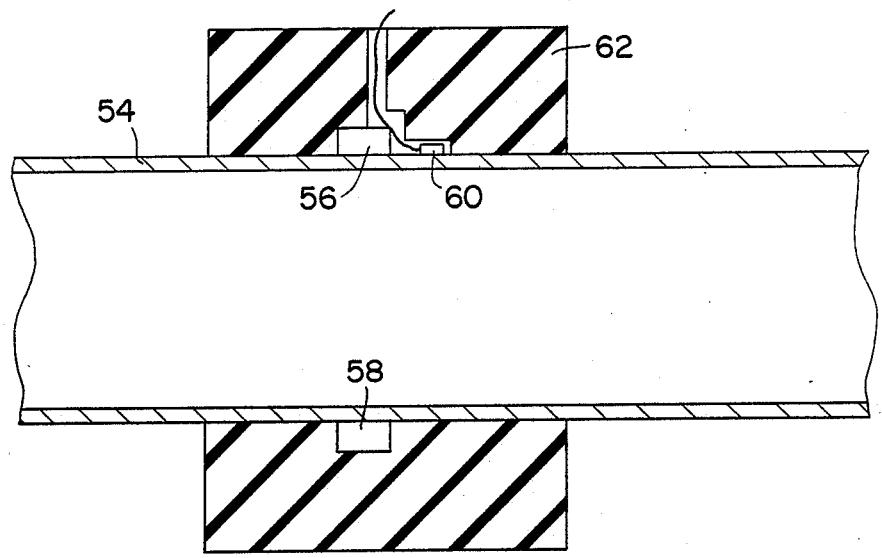
FIG. 4 is a cross-section of the monitor used in FIG. 3.

In FIG. 3, beer of a known o.g. in tank 40 is mixed with water from tank 42 in a mixer 44 of known type. The flows are controlled by respective valves 46, 48, the beer control valve 46 normally being set at a constant flow rate and the water control valve 48 being varied as part of a feedback loop. The product passes from the mixer 44 through a flow meter 50 and monitor 52. The monitor 52 acts to measure the temperature and sonic velocity of the product, generate a temperature-compensated sonic velocity, and supply this as a feedback signal to the valve 48. A similar monitor 54 may be provided to check that beer flowing from the tank 40 is of the stated o.g. FIG. 4 shows in greater detail the monitor 52 mounted on a pipe 54. The monitor comprises an ultrasonic transmitter transducer 56, an oppositely-disposed receive transducer 58, and a thermistor 60, all secured to the exterior of the pipe 54 and enclosed in thermal insulation such as an expanded polystyrene sleeve 62. The relationship between the wall thickness and ultrasonic frequency and the mode of use of the ultrasonic transducers is as described in the above-mentioned publications.

Figure 5:
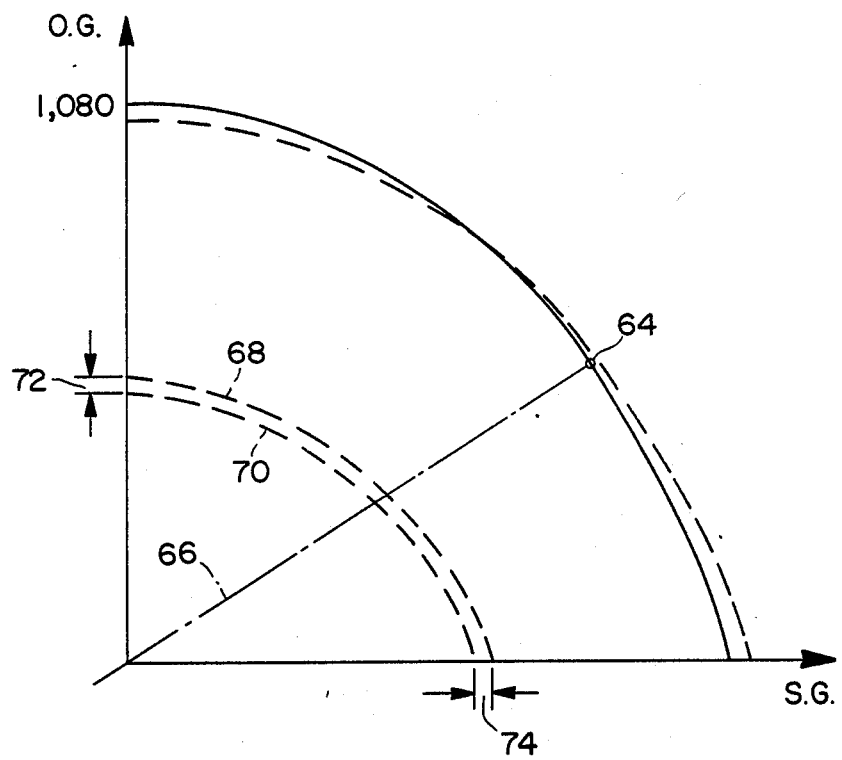
FIG. 5 is a graph, similar to FIG. 2, illustrating the operation of the apparatus of FIG. 3.

FIG. 5, which is a graph similar to FIG. 2, illustrates the operation of the apparatus of FIGS. 3 and 4. The beer in tank 40 has a known o.g. and a known s.g. (measured, for example, by hydrometer) and is thus defined by point 64. Dilution with water causes the characteristics of the product to move along the chain-dotted line 66. By maintaining the temperature-corrected ultrasonic count within the curves 68 and 70, a product is achieved which is equivalent to a beer of o.g. at area 72 and alcohol content at area 74.

It will be appreciated that FIG. 3 shows only the apparatus used when operating as a continuous process. For starting up the process, additional apparatus (not shown) may be required, such as means for feeding product back to the mixer until a relatively stable control feedback is achieved.

Figure 6:
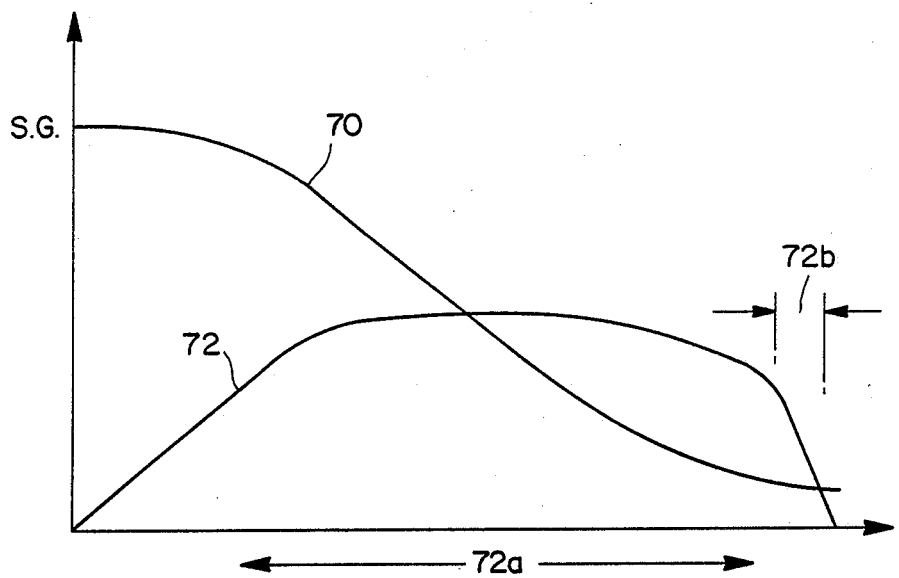
FIG. 6 shows graphs of temperature and s.g. against time in a brewing process.

A further application of the present invention is to the brewing process itself. In FIG. 6, the curve 70 shows s.g. against time and the curve 72 temperature against time during the brewing process (which typically proceeds for a period of 3–5 days). It s conventional to monitor temperature continuously and to apply cooling to the fermenting vessel during the period 72a to limit the maximum temperature. It is also conventional to remove samples from the vessel from time to time to measure s.g. by hydrometer; when a desired s.g. has been reached, the temperature is forced down by additional cooling (period 72b) to teminate fermentation.

Previous attempts to measure s.g. during fermentation by ultrasonic techniques without drawing off samples have been unsuccessful, owing to the presence of gas bubbles and yeast and other solids.

An embodiment of the present invention overcomes these problems by means of a statistical technique. The fermentation period is divided into a number of relatively short time periods, and within each time period a relatively large number of measurements are taken. Suitably the apparatus of FIG. 1 is used and each recorded measurement is the number of pulses passing in a predetermined time interval; such number of pulses is referred to hereinafter as a "count". In the presently preferred embodiment for use with beer, the fermentation is divided into time periods of four minutes, and in each period eight thousand counts are taken.

Figure 7:
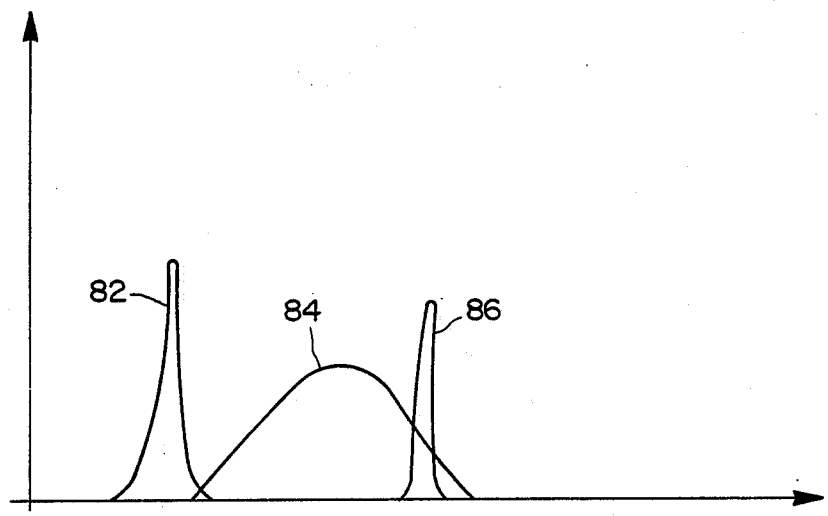

FIG. 7 illustrates typical statistical distributions for three time periods at different points in the fermentation process. Curve 82 is at an early stage and shows a sharply defined peak. Curve 84 is at a later stage with a high degree to gas generation, and shows a much greater variance. Curve 86 is towards the end of the process where gas evolution has almost ceased, and the variance is again much smaller.

In each case, however, the applicants have established that the distribution contains information which can be used to derive actual s.g. at that time period, and other data. It has been found that the minimum point of the distribution is a function of both s.g. and o.g., and of temperature. Given the relationship between s.g. and o.g. discussed above, and given that o.g. for a particular liquor is known, it is therefore possible to determine s.g. at each time period as fermentation proceeds.

The relationships between these variables can be established empirically by building up a library of data by measuring s.g. by hydrometer for various o.g., temperature and ultrasonic count values. Once such a library is available, it is possible to measure s.g. automatically in an on-line and non-intrusive manner.

The distribution information also provides the possibility of automatically measuring other factors during brewing. As indicated above, the spread of the distribution is affected by outgassing; it is also affected by suspended solids. Similar empirical techniques may be used to quantify these effects, and thus provide on-line data relating to these factors.

It will be apparent that the counts can be stored in digital form and their minima and spread derived in a computer by techniques which are well-known and will therefore note be described here.

We claim:

1. A method of determining the specific gravity of a fermentable liquor during fermentation having more than two components and consisting of variable proportions of water, alcohol, dissolved fermentable sugars, yeast solids, and carbon dioxide, the method comprising the steps of fermenting the liquor:

establishing a set of data defining the relationship, at a standard temperature, between constant sonic velocities in fermentable liquors of varying original gravities, measuring the original gravity of a given fermentable liquor before fermentation thereof commences.

fermenting said given fermentable liquor, measuring the velocity of sound in said given fermentable liquor at a given point in time following commencement of fermentation of said given fermentable liquor, measuring the temperature of said given fermentable liquor at said point in time, and deriving from said measured velocity and said measured temperature and said set of data the specific gravity of said given fermentable liquor at said given point in time.

2. A method of determining the specific gravity of a given fermentable liquor having more than two components and consisting of variable proportions of water, alcohol, dissolved fermentable sugars, yeast solids, and carbon dioxide by the second method of claim 1, as fermentation of said given fermentable liquor proceeds, in which:

the time required for said fermentation is divided into a number of time periods each of which is short in relation to the time required for said fermentation, in each said time period a statistically significant number of measurements are made of sonic velocity in said given fermentable liquor, the maximum sonic velocity during each given said time period is established, and the specific gravity of said given fermentable liquor during each given said time period is derived using said maximum velocity as said measured velocity.

3. The method of claim 2, in which the statistical distribution of said statistically significant number of measurements of sonic velocity in said given fermentable liquor in a given said time period is analysed and the spread of said statistical distribution is used as a measure of at leasst one of solids content and outgassing in said given fermentable liquor in the given said time period.

4. The method of claim 1, in which the given fermentable liquor is contained within a containment defined by a wall, and the sonic velocity in said given fermentable liquor is measured by means of ultrasonic sensors positioned on the exterior of said wall.

5. The method of claim 4, in which said temperature measurement is made by means of a sensor attached to the exterior of said wall and within a thermal insulation.

6. A method of diluting a fermented liquor, said method comprising the steps of:

supplying said fermented liquor to a mixing vessel at a known rate, supplying water to said mixing vessel at a controlled rate, mixing said supplied fermented liquor with said supplied water in said mixing vessel to form a product consisting of dilute fermented liquor, measuring the specific gravity of the product resulting from said mixing, the specific gravity of said product being measured by the method of claim 1, and controlling the rate of supply of water to said mixing vessel in dependence on the measurement of specific gravity of the product resulting from the said mixing to form a product of controlled dilution.

* * * * *